(12) United States Patent
Taylor et al.

(10) Patent No.: US 10,717,729 B2
(45) Date of Patent: Jul. 21, 2020

(54) THIAMINE-ORGANIC ACID SALT

(71) Applicant: Purdue Research Foundation, West Lafayette, IN (US)

(72) Inventors: Lynne S Taylor, West Lafayette, IN (US); Lisa J Mauer, West Lafayette, IN (US); Vivekanand Bhardwaj, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/423,321

(22) Filed: May 28, 2019

(65) Prior Publication Data

US 2019/0367498 A1 Dec. 5, 2019

Related U.S. Application Data

(60) Provisional application No. 62/680,820, filed on Jun. 5, 2018.

(51) Int. Cl.
*C07D 417/06* (2006.01)
*C07C 55/10* (2006.01)
*C07C 51/41* (2006.01)
*C07D 213/80* (2006.01)
*C07C 57/13* (2006.01)

(52) U.S. Cl.
CPC ............ *C07D 417/06* (2013.01); *C07C 51/41* (2013.01); *C07C 55/10* (2013.01); *C07C 57/13* (2013.01); *C07D 213/80* (2013.01)

(58) Field of Classification Search
CPC .................................................. C07D 239/42
See application file for complete search history.

(56) References Cited

U.S. PATENT DOCUMENTS 3,432,504 A    3/1969  Goetze Claren

FOREIGN PATENT DOCUMENTS

GB    768773    2/1957

OTHER PUBLICATIONS

Joo, Y et al., A nonconjugated radical polymer glass with high electrical conductivity, Science, 359, 1391-1395 (2018).

*Primary Examiner* — Susanna Moore
(74) *Attorney, Agent, or Firm* — Purdue Research Foundation; Zhigang Rao

(57) ABSTRACT

The present disclosure relates to novel thiamine-organic acid salt, and the method of making the novel thiamine-organic acid salt.

7 Claims, No Drawings

THIAMINE-ORGANIC ACID SALT

CROSS-REFERENCE TO RELATED APPLICATION

This application claims the benefits of U.S. Provisional Application Ser. No. 62/680,820, filed Jun. 5, 2018, the contents of which are incorporated herein entirely

GOVERNMENT SUPPORT CLAUSE

This invention was made with government support under 2016-67017-24592 awarded by the United States Department of Agriculture. The government has certain rights in the invention.

TECHNICAL FIELD

The present disclosure relates to novel thiamine-organic acid salt, and the method of making the novel thiamine-organic acid salt.

BACKGROUND

This section introduces aspects that may help facilitate a better understanding of the disclosure. Accordingly, these statements are to be read in this light and are not to be understood as admissions about what is or is not prior art.

Thiamine, or vitamin B 1, is widely added to foods and to vitamin tablets. Two solid state forms are currently used commercially: thiamine chloride hydrochloride and thiamine mononitrate. Thiamine chloride hydrochloride is quite hygroscopic and is typically used in liquid formulations. Because thiamine mononitrate is less hygroscopic, it is used in food powders as a preferred salt over thiamine chloride hydrochloride.

The thiamine molecule contains two groups capable of ready formation of salts, as may be seen in the following formula:

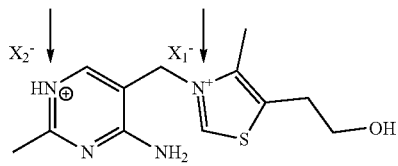 [SMILES: Cc1nc(N)c(C[n+]2csc(CCO)c2C)c[nH+]1]

First, the quaternary nitrogen in the thiazole ring of the molecule requires the presence of an anion, here referred to as anion of $X_1$ so that the molecule can achieve electrical neutrality. Molecules containing only this anion are referred to in this discussion as mono salts of thiamine.

Secondly, the pyrimidine nitrogen distant to the amino group may act as a weak base and combine with an equivalent of acid, thereby acquiring a second anion group, here referred to as $X_2$. Molecules with both as anion of $X_1$ and $X_2$ are referred as di salts of thiamine.

It is well known that a desired inorganic thiamine salt may readily be prepared in high yield and in substantially pure form from another inorganic thiamine salt This is accomplished by reacting the original thiamine salt with a substance yielding the anions desired in the final product and causing the precipitation of the desired product from the reaction mixture.

However, there were very few report for thiamine salt of organic acids, especially pharmaceutically acceptable organic acids. P. H. Stahl and C. G. Wermuth, editors, *Handbook of Pharmaceutical Salts*: Properties, Selection and Use, Weinheim/Zürich: Wiley-VCH/VHCA, 2002. It may be for the reason that the unique structure of thiamine makes it difficult to form stable organic acid salts, especially a stable crystal form of a thiamine/organic acid salt. The U.S. Pat. No. 3,432,504 disclosed thiamine/furan carboxylic mono salts and thiamine/furan dicarboxylic di-salts.

Therefore, there is still a need for novel and stable thiamine salts, crystals, and/or co-crystals of pharmaceutically acceptable organic acids, and the method of making and using the novel and stable thiamine salts, crystals, and/or co-crystals.

SUMMARY

The present disclosure relates to novel thiamine-organic acid salt, and the method of making the novel thiamine-organic acid salt.

In one embodiment, the present disclosure provides a thiamine-organic acid salt of formula I:

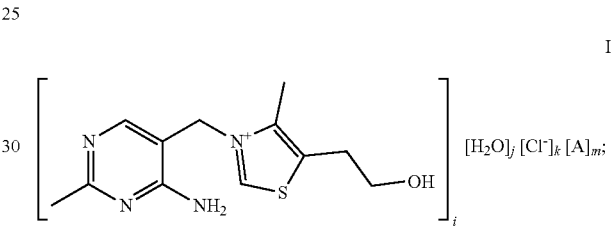

wherein A represents an organic acid moiety comprising two [—COO⁻] groups, or an organic acid moiety comprising one —COOH group and one —COO— group, or a nicotinate group;
i is 1 to 4;
j is 1 to 12;
k is 0-4; and
m is 1-2,
wherein i=k+2 when $[A]_m$ represents one organic acid moiety comprising two [—COO⁻] groups or two organic acid moiety each comprising one —COOH group and one —COO⁻ group, or i=k+1 when $[A]_m$ represents one organic acid moieties comprising one —COOH group and one —COO— group, or a nicotinate group.

In one embodiment, the present disclosure provides a method of making the thiamine-organic acid salt of formula I.

DETAILED DESCRIPTION

For the purposes of promoting an understanding of the principles of the present disclosure, reference will now be made to the embodiments. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

The present disclosure for the first time identified some unique and stable thiamine and organic acid salts.

In one embodiment, the present disclosure provides a thiamine-organic acid salt of formula I:

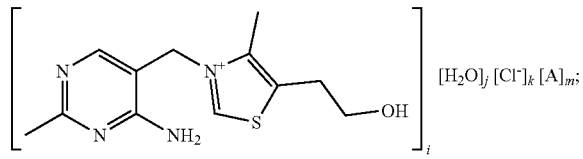

wherein A represents an organic acid moiety comprising two [—COO⁻] groups, or an organic acid moiety comprising one —COOH group and one —COO— group, or a nicotinate group;
i is 1 to 4;
j is 1 to 12;
k is 0-4; and
m is 1-2,
wherein i=k+2 when $[A]_m$ represents one organic acid moiety comprising two [—COO⁻] groups or two organic acid moiety each comprising one —COOH group and one —COO⁻ group, or i=k+1 when $[A]_m$ represents one organic acid moieties comprising one —COOH group and one —COO⁻ group, or a nicotinate group.

In one embodiment, the present disclosure provides a thiamine-organic acid salt of formula I:

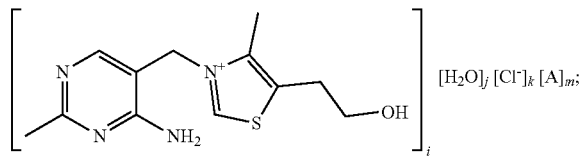

wherein A represents [(⁻OOC)-L-(COO⁻)], or [(⁻OOC)-L-(COOH)], or a nicotinate group, and L is $C_0$-$C_8$ saturated or unsaturated hydrocarbon linker;
i is 1 to 4;
j is 1 to 12;
k is 0-4; and
m is 1-2,
wherein i=k+2 when $[A]_m$ represents one organic acid moiety comprising two [—COO⁻] groups or two organic acid moiety each comprising one —COOH group and one —COO⁻ group, or i=k+1 when $[A]_m$ represents one organic acid moiety comprising one —COOH group and one —COO— group, or a nicotinate group.

In one embodiment, the present disclosure provides a thiamine-organic acid salt of formula I:

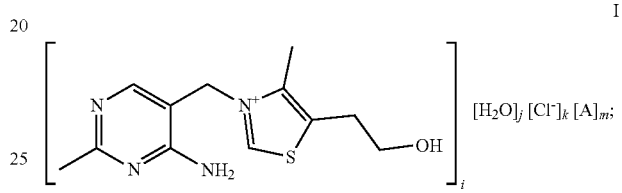

wherein A represents [(⁻OOC)-L-(COO⁻)] or [(⁻OOC)-L-(COOH)], or a nicotinate group, and L is a bond, —CH₂—, —CH₂—CH₂—, or —CH═CH—; i is 2 or 4; j is 1-10, and k is 0, 1, or 2.

In one embodiment, the present disclosure provides a thiamine-organic acid salt of formula I, wherein the thiamine-organic acid salt is selected from the group consisting of:

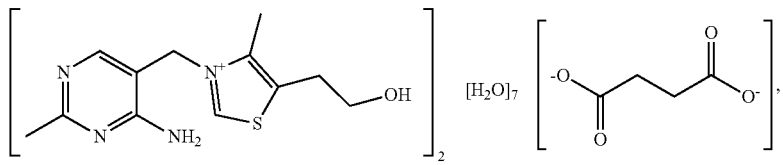

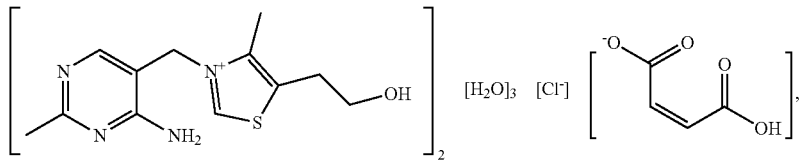

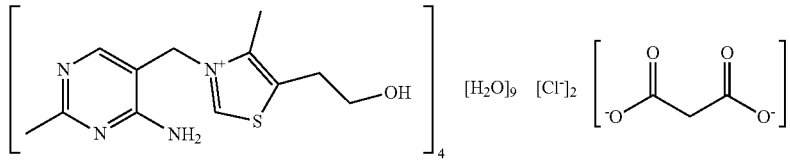

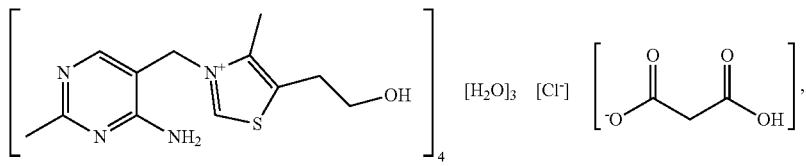

-continued

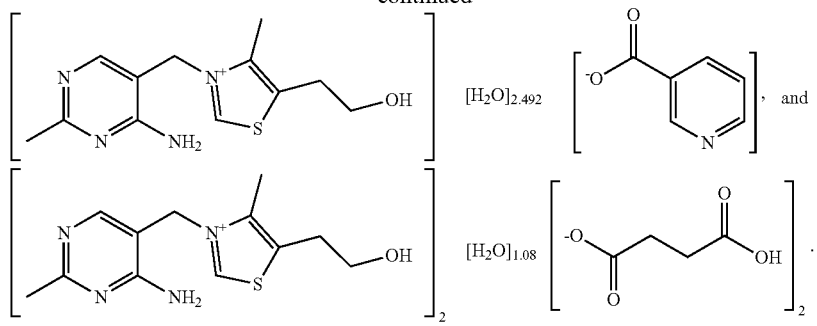

In one embodiment, the present disclosure provides a method of making the thiamine-organic acid salt of formula I, wherein the method comprises:

a) preparing a silver salt $Ag_2A$ or $AgA$, wherein A represents an organic acid moiety comprising two [—$COO^-$] groups in the silver salt $Ag_2A$ and wherein A represents an organic acid moiety comprising a nicotinate group or an organic acid moiety comprising one [—$COO^-$] group and one [—COOH] groups in the silver salt AgA;

b) preparing a solution comprising thiamine cations and A by contacting a aqueous solution comprising thiamine chloride with the silver salt prepared in step a); and c) preparing thiamine-organic acid salt by adding the solution comprising thiamine cations and A prepared in step b) to an organic solvent, and allowing the crystal of the thiamine salt/hydrate of claim 1 to nucleate and grow.

In one embodiment, the present disclosure provides a method of making the thiamine-organic acid salt of formula I, wherein the organic solvent may be but is not limited to acetone; tetrahydrofuran; aliphatic alcohols such as methanol, ethanol, isopropanol, butanol; esters such as ethyl acetate; ethers; alkanes such as hexane, heptane, or cyclohexane; halogenated solvents such as dichloromethane, chloroform, or carbon tetrachloride, or any combination thereof. In one aspect, the preferred solvent is acetone or tetrahydrofuran.

EXPERIMENTS

Single Crystal X-Ray Diffraction (SXD) analysis

Single crystal diffraction data were collected on a Bruker AXS D8 Quest diffractometer with a CMOS detector and graphite monochromated Mo Kα ($\lambda$=0.71073 Å) or Cu Kα ($\lambda$=1.54178 Å) radiation with an Oxford Cryosystem 800 temperature controller operating at 150 (±2) K. Diffraction data were processed (cell refinement and data reduction) using Bruker Apex3 v2016.9-0 (Bruker, 2016), SAINT V8.37A (Bruker, 2016) software and structure solution and refinement were carried out by using SHELXS97 (Sheldrick, 2008), SHELXL2017/1 (Sheldrick, 2017), SHELXLE Rev859 (Hübschle et al., 2011).

Thermogravimetric Analysis

The weight loss profile as a function of heating a sample (thermogravimetric analysis) was generated using Q50 TGA (TA Instruments, New Castle, Del.). Approximately 3-6 mg sample was placed onto aluminum pans before loading onto platinum sample holders. Samples were heated from room temperature to 300° C. at the rate of 5° C./min. The furnace was purged with nitrogen gas. The thermogravimetric profile was plotted using the using the TA Universal Analysis software (TA Instruments, New Castle, Del.).

Dynamic Vapor Sorption (DVS)

Moisture sorption profiles were generated at 25° C. using an SGA-100 symmetrical gravimetric analyzer (TA Instrument, New Castle, Del.). The samples (5-20 mg) were exposed to 25% to 95% relative humidity (RH) at step size of 5% RH and from 95 to 99% RH at step size of 1% RH, with a maximum step time of 360 min. The equilibrium criteria were set to change of mass of less than 0.01% (w/w) for 5 min for each step. Nitrogen was used as the purge gas.

Example 1: Thiamine Succinate: Dithiamine Succinate Heptahydrate

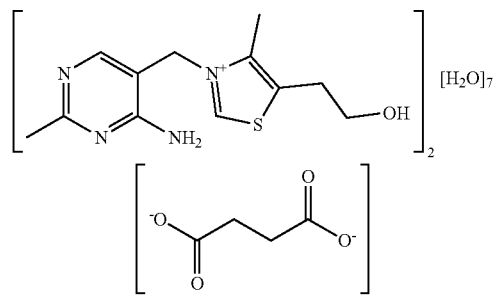

Step 1: Preparation of Silver Succinate:

About 10 mmoles of disodium succinate hexahydrate was dissolved in approximately 6 ml water in a 20 mL glass vial. Two mL of a 5M solution of silver nitrate (10 mmoles) was added to the succinate solution with stirring. Silver succinate was formed as white precipitates which were collected on Nylon filters (Millipore, 0.2 µm pore size) over a Buchner funnel. Vacuum was applied to accelerate the filtration process. The precipitates were washed 4 times with ~2-3 mL of deionized water. The white precipitates so obtained were dried in an oven for 1 hour at 50° C., and stored protected from light to prevent discoloration (silver compounds are prone to discoloration on exposure to light).

Step 2: Preparation of Thiamine Chloride:

About one molar equivalent of thiamine chloride hydrochloride dissolved in water was mixed with one molar equivalent of sodium hydroxide and the resulting thiamine chloride was crystallized by addition of acetone to the aqueous solution. The thiamine chloride so obtained was purified by recrystallization from water-acetone mixture.

Step 3: Preparation of Thiamine Succinate:

About 576 mg thiamine chloride was dissolved in 3 ml water and 300 mg of silver succinate was added to this solution. The suspension obtained was centrifuged at 7200 g for 3 minutes and the resulting supernatant containing the thiamine cations and succinate anions was filtered through a Nylon filter (Millipore, 0.2 μm pore size).

Step 4: Crystallization of Thiamine Succinate:

Approximately one ml of the thiamine succinate solution prepared in Step 3 was added dropwise to 10 ml of acetone in a 20 mL vial. The solution was stored in the freezer (−20° C.) for 1 week. Needle shaped transparent crystals were obtained in the vial with 1:10 water-acetone. One of these crystals was used for single crystal XRD analysis, and was identified as Example 1: dithiamine succinate heptahydrate.

TABLE 1

Experimental details for Example 1 single crystal XRD

| Sample name | Example 1 |
|---|---|
| Crystal data | |
| Chemical formula | $2(C_{12}H_{17}N_4OS) \cdot C_4H_4O_4 \cdot 7(H_2O)$ |
| $M_r$ | 772.89 |
| Crystal system, space group | Triclinic, P⁻1 |
| Temperature (K) | 150 |
| a, b, c (Å) | 11.1565 (3), 12.5014 (4), 14.1668 (4) |
| α, β, λ(°) | 108.7195 (13), 90.1747 (15), 90.2162 (15) |
| V (Å³) | 1871.32 (10) |
| Z | 2 |
| Radiation type | Cu Kα |
| $\mu$ (mm⁻¹) | 1.91 |
| Crystal size (mm) | 0.55 × 0.21 × 0.09 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.462, 0.754 |
| No. of measured, independent and observed [I > 2σ (I)] reflections | 34701, 7827, 6994 |
| $R_{int}$ | 0.087 |
| $(\sin \theta/\lambda)_{max}$ (Å⁻¹) | 0.639 |
| Refinement | |
| $R[F^2 > 2\sigma(F^2)]$, $wR(F^2)$, S | 0.051, 0.146, 1.08 |
| No. of reflections | 7827 |
| No. of parameters | 511 |
| No. of restraints | 14 |
| H-atom treatment | H atoms treated by a mixture of independent and constrained refinement |
| $\Delta\rho_{max}$, $\Delta\rho_{min}$ (e Å⁻³) | 0.50, −0.51 |

TABLE 2

Examples 2-5 were prepared with essentially the same method of making Example 1.

| Example No. | Thiamine-organic acid salt | | | Solvent for crystallization |
|---|---|---|---|---|
| 2 | [thiamine cation]₂ | [H₂O]₃ | [Cl⁻] | [maleate] | tetrahydrofuran |
| 3 | [thiamine cation]₄ | [H₂O]₉ | [Cl⁻]₂ | [malonate dianion] | acetone |
| 4 | [thiamine cation]₂ | [H₂O]₃ | [Cl⁻] | [malonate monoanion] | tetrahydrofuran |
| 5 | [thiamine cation]₂ | [H₂O]₂.₅ | | [nicotinate] | acetone |

TABLE 3

Experimental details for Example 2 single crystal XRD

| Sample name | Example 2 |
|---|---|
| Crystal data | |
| Chemical formula | $2(C_{12}H_{17}N_4OS) \cdot C_4H_3O_4 \cdot Cl \cdot 3(H_2O)$ |
| $M_r$ | 735.27 |
| Crystal system, space group | Triclinic, $P^{-}1$ |
| Temperature (K) | 150 |
| a, b, c (Å) | 11.6913 (6), 12.9090 (6), 13.2717 (7) |
| α, β, λ (°) | 114.5680 (16), 105.6584 (18), 95.3322 (19) |
| V (Å$^3$) | 1705.25 (15) |
| Z | 2 |
| Radiation type | Mo Kα |
| μ (mm$^{-1}$) | 0.30 |
| Crystal size (mm) | 0.55 × 0.33 × 0.28 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.705, 0.747 |
| No. of measured, independent and observed [I > 2σ (I)] reflections | 124509, 13011, 10187 |
| $R_{int}$ | 0.032 |
| $(\sin\theta/\lambda)_{max}$ (Å$^{-1}$) | 0.771 |
| Refinement | |
| $R[F^2 > 2\sigma(F^2)]$, $wR(F^2)$, S | 0.038, 0.111, 1.03 |
| No. of reflections | 13011 |
| No. of parameters | 549 |
| No. of restraints | 261 |
| H-atom treatment | H atoms treated by a mixture of independent and constrained refinement |
| $\Delta\rangle_{max}$, $\Delta\rangle_{min}$ (e Å$^{-3}$) | 0.42, −0.36 |

TABLE 4

Experimental details for Example 3 single crystal XRD

| Sample name | Example 3 |
|---|---|
| Crystal data | |
| Chemical formula | $4(C_{12}H_{17}N_4OS) \cdot C_3H_2O_4 \cdot 2(Cl) \cdot 9(H_2O)$ |
| $M_r$ | 1396.51 |
| Crystal system, space group | Monoclinic, $P2_1/c$ |
| Temperature (K) | 150 |
| a, b, c (Å) | 11.9760 (8), 27.1164 (17), 11.1581 (7) |
| A, β, λ (°) | 111.359 (2) |
| V (Å$^3$) | 3374.7 (4) |
| Z | 2 |
| Radiation type | Mo Kα |
| μ (mm$^{-1}$) | 0.30 |
| Crystal size (mm) | 0.43 × 0.11 × 0.03 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.601, 0.746 |
| No. of measured, independent and observed [I > 2σ (I)] reflections | 35002, 8187, 6997 |
| $R_{int}$ | 0.053 |
| $(\sin\theta/\lambda)_{max}$ (Å$^{-1}$) | 0.667 |
| Refinement | |
| $R[F^2 > 2\sigma(F^2)]$, $wR(F^2)$, S | 0.089, 0.215, 1.15 |
| No. of reflections | 8187 |
| No. of parameters | 517 |
| No. of restraints | 39 |
| H-atom treatment | H atoms treated by a mixture of independent and constrained refinement $w = 1/[\sigma^2(F_o^2) + 21.0624P]$ where $P = (F_o^2 + 2F_c^2)/3$ |
| $\Delta\rangle_{max}$, $\Delta\rangle_{min}$ (e Å$^{-3}$) | 0.88, −0.94 |

TABLE 5

Experimental details for Example 4 single crystal XRD

| Sample name | Example 4 |
|---|---|
| Crystal data | |
| Chemical formula | $2(C_{12}H_{17}N_4OS) \cdot C_3H_3O_4 \cdot Cl \cdot 3(H_2O)$ |
| $M_r$ | 723.26 |
| Crystal system, space group | Triclinic, $P^{-}1$ |
| Temperature (K) | 150 |
| a, b, c (Å) | 6.5349 (4), 11.2514 (7), 12.3863 (8) |
| A, β, λ (°) | 113.370 (2), 91.661 (2), 92.763 (2) |
| V (Å$^3$) | 833.89 (9) |
| Z | 1 |
| Radiation type | Mo Kα |
| μ (mm$^{-1}$) | 0.30 |
| Crystal size (mm) | 0.55 × 0.42 × 0.16 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.684, 0.747 |
| No. of measured, independent and observed [I > 2σ (I)] reflections | 44039, 6337, 5585 |
| $R_{int}$ | 0.029 |
| $(\sin\theta/\lambda)_{max}$ (Å$^{-1}$) | 0.771 |
| Refinement | |
| $R[F^2 > 2\sigma(F^2)]$, $wR(F^2)$, S | 0.032, 0.087, 1.07 |
| No. of reflections | 6337 |
| No. of parameters | 276 |
| No. of restraints | 7 |
| H-atom treatment | H atoms treated by a mixture of independent and constrained refinement |
| $\Delta\rangle_{max}$, $\Delta\rangle_{min}$ (e Å$^{-3}$) | 0.47, −0.33 |

TABLE 6

Experimental details for Example 5 single crystal XRD

| | |
|---|---|
| Crystal data | |
| Chemical formula | $C_{12}H_{17}N_4OS \cdot C_6H_4NO_2 \cdot 2.5(H_2O)$ |
| $M_r$ | 432.39 |
| Crystal system, space group | Triclinic, P1 |
| Temperature (K) | 120 |
| a, b, c (Å) | 13.0410 (7), 13.4469 (6), 15.5094 (8) |
| α, β, γ (°) | 113.0211 (17), 95.2862 (18), 110.5348 (16) |
| V (Å$^3$) | 2259.6 (2) |

TABLE 6-continued

Experimental details for Example 5 single crystal XRD

| | |
|---|---|
| Z | 4 |
| Radiation type | Mo Kα |
| $\mu$ (mm$^{-1}$) | 0.18 |
| Crystal size (mm) | 0.22 × 0.20 × 0.13 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.597, 0.746 |
| No. of measured, independent and observed [I > 2σ(I)] reflections | 28170, 10518, 7599 |
| $R_{int}$ | 0.059 |
| (sin θ/λ)$_{max}$ (Å$^{-1}$) | 0.667 |
| Refinement | |
| R[F$^2$ > 2σ(F$^2$)], wR(F$^2$), S | 0.070, 0.209, 1.03 |
| No. of reflections | 10518 |
| No. of parameters | 871 |
| No. of restraints | 1183 |
| H-atom treatment | H atoms treated by a mixture of independent and constrained refinement |
| $\Delta\rho_{max}$, $\Delta\rho_{min}$ (e Å$^{-3}$) | 0.67, −0.48 |

Example 6: Thiamine Succinate: Dithiamine di(H-succinate) Monohydrate

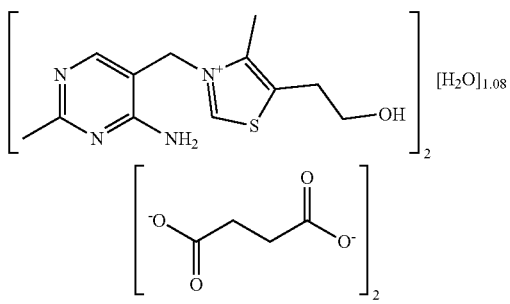

In an analytical column, approximately 13 g of Amberlyst A26 OH form (Sigma Millipore) anion exchange resin was packed by gravity settling. The supplied hydroxyl anions were replaced by succinate anions with an aqueous solution of approximately 0.5M succinic acid (equivalent to 4.8 g succinic acid). The column was washed with approximately 100 mL purified water to remove unbound succinate. In the final step, 3 mL of 1M thiamine chloride solution was used to replace succinate in the anion column with chloride. The eluted solution containing thiamine cation and succinate anions was air dried at room temperature.

TABLE 7

Experimental details for Example 6 single crystal XRD

| | |
|---|---|
| Sample name | Example 7 |
| Crystal data | |
| Chemical formula | 2(C$_4$H$_5$O$_4$)·2(C$_{12}$H$_{17}$N$_4$OS)·1.08(H$_2$O) |
| $M_r$ | 784.33 |

TABLE 7-continued

Experimental details for Example 6 single crystal XRD

| | |
|---|---|
| Sample name | Example 7 |
| Crystal system, space group | Triclinic, P1 |
| Temperature (K) | 150 |
| a, b, c (Å) | 10.4215 (4), 11.8581 (5), 16.4524 (7) |
| α, β, γ (°) | 91.9602 (13), 97.7888 (13), 114.2350 (11) |
| V (Å$^3$) | 1827.78 (13) |
| Z | 2 |
| Radiation type | Cu Kα |
| $\mu$ (mm$^{-1}$) | 1.93 |
| Crystal size (mm) | 0.21 × 0.20 × 0.16 |
| Data collection | |
| Diffractometer | Bruker AXS D8 Quest CMOS diffractometer |
| Absorption correction | Multi-scan SADABS 2016/2: Krause, L., Herbst-Irmer, R., Sheldrick G. M. & Stalke D., J. Appl. Cryst. 48 (2015) 3-10 |
| $T_{min}$, $T_{max}$ | 0.570, 0.754 |
| No. of measured, independent and observed [I > 2σ(I)] reflections | 20997, 7328, 6372 |
| $R_{int}$ | 0.036 |
| (sin θ/λ)$_{max}$ (Å$^{-1}$) | 0.640 |
| Refinement | |
| R[F$^2$ > 2σ(F$^2$)], wR(F$^2$), S | 0.055, 0.167, 1.18 |
| No. of reflections | 7328 |
| No. of parameters | 600 |
| No. of restraints | 321 |
| H-atom treatment | H atoms treated by a mixture of independent and constrained refinement |
| $\Delta\rho_{max}$, $\Delta\rho_{min}$ (e Å$^{-3}$) | 0.39, −0.47 |

Computer programs for XRD: Apex3 v2016.9-0 (Bruker, 2016), SAINT V8.37A (Bruker, 2016), SHELXS97 (Sheldrick, 2008), SHELXL2017/1 (Sheldrick, 2015, 2017), SHELXLE Rev859 (Hübschle et al., 2011).

In thermogravimetric analysis, all the new salts/co-crystals disclosed here exhibit weight loss which can be attributed to chemical degradation at a lower temperature than the Cl, Cl—HCl, or NO$_3$ salts. However, the degradation starts at a temperature no lower than 130, 105, and 115° C. for succinate, H-maleate Cl, and H-malonate Cl respectively. This allows their use as food additives.

Regarding dynamic moisture sorption, thiamine mononitrate is practically non-hygroscopic, but is considerably less soluble in water (2.7 g/100 ml) than the Cl (>30 g/100 ml) or Cl—HCl (>50 g/100 ml) salts. Thiamine Cl and Thiamine Cl HCl are very soluble, and show high hygroscopicity at 88%, and 95% RH, respectively. However, both these compounds exhibit instability in solution. The hygroscopic behaviour of new salts disclosed in the present disclosure is comparable to thiamine Cl—HCl, with elevated hygroscopicity seen at >95% RH for H-maleate Cl and 88% RH for H-malonate Cl.

Additional disclosure is found in Appendix A, filed herewith, entirety of which is incorporated herein by reference into the present disclosure Those skilled in the art will recognize that numerous modifications can be made to the specific implementations described above. The implementations should not be limited to the particular limitations described. Other implementations may be possible.

We claim:

1. A thiamine-organic acid salt of formula I:

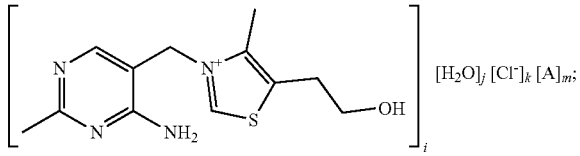

wherein A represents an organic acid moiety comprising two [—COO⁻] groups, or an organic acid moiety comprising one —COOH group and one —COO— group, or a nicotinate group;

i is 1 to 4;
j is 1 to 12;
k is 0-4; and
m is 1-2, wherein i=k+2 when [A]$_m$ represents one organic acid moiety comprising two [—COO⁻] groups or two organic acid moiety each comprising one —COOH group and one —COO⁻ group, or i=k+1 when [A]$_m$ represents one organic acid moiety comprising one —COOH group and one —COO⁻ group, or a nicotinate group.

2. The thiamine-organic acid salt of claim 1, wherein A represents [(⁻OOC)-L-(COO⁻)], or [(⁻OOC)-L-(COOH)], or a nicotinate group, and L is $C_0$-$C_8$ saturated or unsaturated hydrocarbon linker.

3. The thiamine-organic acid salt of claim 2, wherein L is a bond, —CH$_2$—, —CH$_2$—CH$_2$—, or —CH═CH—; i is 2 or 4; j is 1-10, and k is 0, 1, or 2.

4. The thiamine-organic acid salt of claim 1, wherein the co-crystal is selected from the group consisting of:

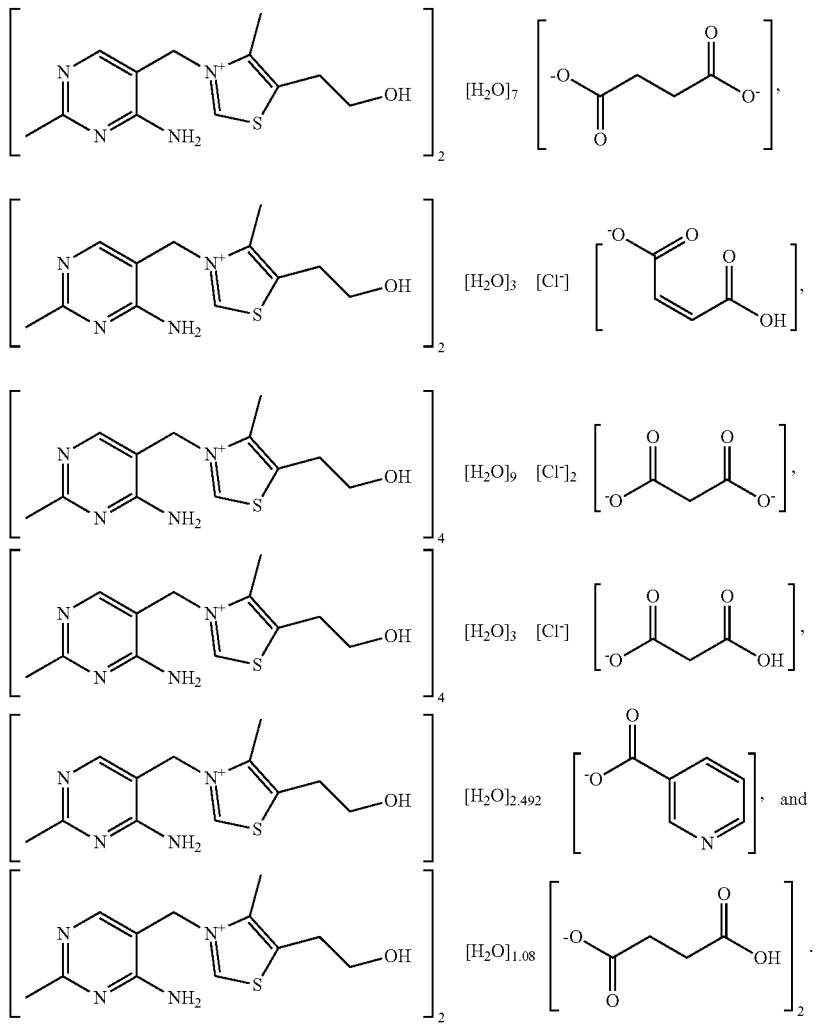

5. The thiamine-organic acid salt of claim 1, wherein the thiamine-organic acid salt is single crystal.

6. A method of making the thiamine-organic acid salt of claim 1, wherein the method comprises:

a) preparing a silver salt Ag$_2$A or AgA, wherein A represents an organic acid moiety comprising two [—COO⁻] groups in the silver salt Ag$_2$A and wherein A represents an organic acid moiety comprising a nicotinate group or an organic acid moiety comprising one [—COO⁻] group and one [—COOH] groups in the silver salt AgA;
- b) preparing a solution comprising thiamine cations and A by contacting an aqueous solution comprising thiamine chloride with the silver salt prepared in step a); and
- c) preparing thiamine-organic acid salt of claim 1 by adding the solution comprising thiamine cations and A prepared in step b) to an organic solvent, and allowing the crystal of the thiamine salt/hydrate of claim 1 to grow.

7. The method of claim 6, wherein the organic solvent is acetone or tetrahydrofuran.

* * * * *